(12) United States Patent
van der Steen et al.

(10) Patent No.: US 11,518,755 B2
(45) Date of Patent: Dec. 6, 2022

(54) STABLE SOLUTIONS OF MULTICYCLIC ANTIDEPRESSANTS

(71) Applicant: Leyden Technologies B.V., Nijmegen (NL)

(72) Inventors: Hans van der Steen, Nijmegen (NL); Karel Jollie, Nijmegen (NL); Willem van Rijn, Nijmegen (NL)

(73) Assignee: Leyden Technologies B.V., Nijmegen (NL)

( * ) Notice: Subject to any disclaimer, the term of this patent is extended or adjusted under 35 U.S.C. 154(b) by 117 days.

(21) Appl. No.: 16/650,049

(22) PCT Filed: Oct. 5, 2018

(86) PCT No.: PCT/EP2018/077121
§ 371 (c)(1),
(2) Date: Mar. 24, 2020

(87) PCT Pub. No.: WO2019/068859
PCT Pub. Date: Apr. 11, 2019

(65) Prior Publication Data
US 2020/0290999 A1 Sep. 17, 2020

(30) Foreign Application Priority Data
Oct. 6, 2017 (EP) .................................. 17195256

(51) Int. Cl.
*C07D 403/04* (2006.01)
*A61K 9/00* (2006.01)
*A61K 9/08* (2006.01)
*A61K 9/48* (2006.01)
*A61K 47/10* (2017.01)

(52) U.S. Cl.
CPC .......... *C07D 403/04* (2013.01); *A61K 9/0019* (2013.01); *A61K 9/0053* (2013.01); *A61K 9/08* (2013.01); *A61K 9/4808* (2013.01); *A61K 47/10* (2013.01)

(58) Field of Classification Search
CPC .................................................. C07D 403/04
See application file for complete search history.

(56) References Cited

FOREIGN PATENT DOCUMENTS

| EP | 1880724 A1 | | 1/2008 |
|---|---|---|---|
| WO | WO 2004/006959 | * | 1/2004 |
| WO | WO2005/007168 A1 | | 1/2005 |
| WO | WO2005/063254 A1 | | 7/2005 |
| WO | WO 2013/100879 | * | 7/2013 |

OTHER PUBLICATIONS

Hemenway, Jeffrey N., et al. "Formation of reactive impurities in aqueous and neat polyethylene glycol 400 and effects of antioxidants and oxidation inducers." Journal of pharmaceutical sciences 101.9 (2012): 3305-3318.
Suma, Ramagiri, Hari Kosanam, and P. K. Sai Prakash. "Stability study of bupropion and olanzapine in formaldehyde solutions." Rapid Communications in Mass Spectrometry: An International Journal Devoted to the Rapid Dissemination of Up-to-the-Minute Research in Mass Spectrometry 20.8 (2006): 1390-1394.
Waterman, Kenneth C., et al. "N-methylation and N-formylation of a secondary amine drug (varenicline) in an osmotic tablet." Journal of pharmaceutical sciences 97.4 (2008): 1499-1507.
Leucht, Stefan, et al. "Second-generation versus first-generation antipsychotic drugs for schizophrenia: a meta-analysis." The Lancet 373.9657 (2009): 31-41.
Seeman, Philip, et al. "Dopamine supersensitivity correlates with D2High states, implying many paths to psychosis." Proceedings of the National Academy of Sciences 102.9 (2005): 3513-3518.
Crilly, John. "The history of clozapine and its emergence in the US market: a review and analysis." History of psychiatry 18.1 (2007): 39-60.
Popovic, Dina, Philippe Nuss, and Eduard Vieta. "Revisiting loxapine: a systematic review." Annals of general psychiatry 14.1 (2015): 15.
Geller, Vadim, et al. "Clotiapine compared with chlorpromazine in chronic schizophrenia." Schizophrenia research 80.2-3 (2005): 343-347.
Haddad, Peter M., Cecilia Brain, and Jan Scott. "Nonadherence with antipsychotic medication in schizophrenia: challenges and management strategies." Patient related outcome measures 5 (2014): 43.
Skibiński, Robert, et al. "Characterization of forced degradation products of clozapine by LC-DAD/ESI-Q-TOF." Journal of pharmaceutical and biomedical analysis 131 (2016): 272-280.

* cited by examiner

*Primary Examiner* — Rei Tsang Shiao
(74) *Attorney, Agent, or Firm* — N.V. Nederlandsch Octrooibureau

(57) ABSTRACT

The invention relates to the field of medicine, specifically the field of atypical antipsychotics. New compositions are provided that provide drug solutions of high stability.

20 Claims, No Drawings

STABLE SOLUTIONS OF MULTICYCLIC ANTIDEPRESSANTS

FIELD OF THE INVENTION

The present invention relates to the field of medicine, specifically the field of atypical antipsychotics. New compositions of high stability are provided, comprising benzazepine drugs with piperazine moieties and a solvent system based on poly(ethylene glycol).

BACKGROUND ART

Atypical antipsychotics are widely known in the art (see e. g. Leucht et al., The Lancet (2009) doi: 10.1016/S0140-6736(08)61764-X, or Seeman, Can. J. Psychiatry (2002) PMID: 11873706). An important subgroup of such antipsychotics is that of benzazepines, particularly dibenzazepines, with piperazine moieties, such as clozapine (Crilly, History of Psychiatry (2007) doi:10.1177/0957154X07070335). Discovered in 1953, clozapine remains on the World Health Organisation model list of Essential Medicines (19$^{th}$ edition, this document is available on the internet at www.whoint/medicines/publications/essentialmedicines). Examples of other piperazine-benzazepines are quetiapine, olanzapine, amoxapine, loxapine, clotiapine, and N-desmethyl metabolites thereof such as norclozapine, norolanzapine, and norquetiapine (see for example Popovic et al., Ann. Gen. Psychiatry (2015) doi: 10.1186/s12991-015-0053-3 and Geller et al., Schizophrenia Research (2005) doi:10.1016/j.schres.2005.07.007). They are often suitable for the treatment of patients showing little to no response to other forms of antipsychotic treatment.

A known disadvantage of piperazine-benzazepines, and piperazine-dibenzazepines in particular, is their very low solubility in water. Enzymes involved in piperazine-benzazepine metabolism have complex pharmacogenetics and thus are diversely expressed throughout the population. This makes precise dosing, tailored to an individual subject, rather important. Fluids are an attractive form of administration, because they allow precise dosing without the need to break pills or capsules to administer low doses when desired. Also, a solution promotes patient compliance in situations where patients have difficulty swallowing, or where concordance is low. This is a particular challenge for antipsychotics for the treatment of for example schizophrenia, due to the association of such conditions with social isolation, stigma, and comorbid substance misuse (Haddad et al., Patient Relat. Outcome Meas. (2014) doi: 10.2147/PROM.S42735). The sensory experience of a solution (particularly its taste) is an important factor in promoting patient compliance, and solvents with foul or unpleasant taste generally decrease compliance.

WO2005/007168 describes the use of a suspension of clozapine. In suspensions the solid particles can sediment and form cakes. The presence of solid particles is a dosing risk because solid particles can stick to pipettes or needles, and are generally not homogeneously distributed throughout the fluid. WO2005/007168 mitigates this problem by using a wetting agent, to promote flocculation. Flocculation is a process where suspended particles agglomerate, forming larger particles that settle loosely and can be re-dispersed with shaking. WO2005063254 discloses a solvent system for neuropsychiatric agents containing 3% benzyl alcohol and 24% ethanol. EP1880724 discloses clozapine, olanzapine, or quetiapine solutions using a solvent system consisting of 1% benzyl alcohol or 1% phenylethylalcohol, made to volume with combinations of PEG300, PEG400, glycerine, triglycerides, ethanol, poloxamer 124, poly(propylene glycol), and/or liquid paraffin.

A disadvantage of piperazine-benzazepines is their susceptibility to decay due to the effect of environmental factors or excipient impurities, leading to acidic, basic, neutral, photo UV-vis, photo UVC, and oxidative stress conditions (Skibinski et al., J. Pharm. Biomed. Anal. (2016) doi: 10.1016/j.jpba.2016.09.007). EP1880724 recognises this problem and describes two precautions, namely the use of water-free solvent systems with a low peroxide content, and the sparging of the solution using nitrogen gas to purge oxygen. This is said to reduce drug decay.

Still, no sufficiently concentrated clozapine solutions are on the market, only solid formulations or suspensions are available. There are no clozapine solutions with a known stability. Given the impact of schizophrenia and other psychotic conditions, there is an ongoing need for stable, homogeneous, and sufficiently concentrated solutions of piperazine-benzazepines.

SUMMARY OF THE INVENTION

In a first aspect, the present invention seeks to provide a composition comprising a solvent system and a substance of general formula (I), which is a piperazine-benzazepine, or a pharmaceutically acceptable salt thereof. The solvent system comprises 70-100% by weight of poly(ethylene glycol) with a number-average molecular weight of 1000 or less, and 0-30% by weight of water. The composition is a solution, and the poly(ethylene glycol) comprises less than 80 μg/g of formaldehyde impurity. In preferred embodiments, the substance of general formula (I) is selected from the group consisting of clozapine, norclozapine, olanzapine, norolanzapine, loxapine, amoxapine, clotiapine, quetiapine, and norquetiapine, or a pharmaceutically acceptable salt thereof, preferably clozapine or a pharmaceutically acceptable salt thereof. In further preferred embodiments, the composition comprises at least 11 mg/mL, preferably at least 50 mg/mL, more preferably at least 70 mg/mL of a substance of general formula (I) or a pharmaceutically acceptable salt thereof. In further preferred embodiments, the poly(ethylene glycol) comprises less than 30 μg/g of formaldehyde impurity. In further preferred embodiments, the composition comprises at most 10 mg/mL by weight of flavouring or sweetening agents such as sucralose or peppermint oil. In further preferred embodiments, the poly(ethylene glycol) has a number-average molecular weight of 200-800, preferably of 200-700, more preferably of 200-600. In further preferred embodiments, the composition further comprises an antioxidant such as a thiosulphate salt, propyl gallate, or a tocopherol. In preferred embodiments, the composition is a pharmaceutical composition, preferably formulated as an injectable preparation, either for subcutaneous, intravenous, or intramuscular administration, or as a solution for oral administration, or as a liquid-filled capsule, preferably a softgel capsule. In preferred embodiments, the composition further comprises a nonionic surfactant. In preferred embodiments, the composition consists essentially of a substance of general formula (I) or a pharmaceutically acceptable salt thereof, and a solvent system consisting essentially of 70-100% by weight poly(ethylene glycol) with a number-average molecular weight of 1000 or less and 0-30% by weight of water, and optionally one or more flavouring or sweetening agent, and optionally one or more antioxidant. In the composition according to the invention, the substance of general formula (I) or the pharmaceutically acceptable salt thereof is stable for at least one month, preferably for at least six months.

In an aspect of the invention, the composition is for use as a medicament, preferably for treatment of psychosis. In preferred embodiments of this aspect, the composition is for oral administration, preferably in a daily dose of at least 6 mg. In preferred embodiments of this aspect, the composition is for administration at least one time per day.

In an aspect of the invention, a method is provided, which is a method of treating, ameliorating, delaying, curing, or stabilizing psychosis, said method comprising the step of administering to a subject in need thereof an effective dose of a composition according to the first aspect of the invention.

DESCRIPTION OF EMBODIMENTS

It has been surprisingly found that dissolution of piperazine-benzazepines in a solvent system comprising 70-100% of a short PEG having very low trace amounts of formaldehyde results in homogeneous solutions of exceptional stability. Therefore, in its first aspect the invention provides a composition comprising a solvent system and a substance of general formula (I)

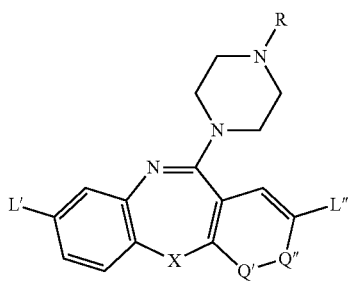

(I)

or a pharmaceutically acceptable salt thereof or optionally a metabolite thereof, wherein
X is —O—, —S—, or —N(H)—,
R is —H, —CH$_3$, or —(CH$_2$)$_2$—O—(CH$_2$)$_2$—OH,
L' and L" are each independently chosen from the group consisting of —H, —CH$_3$, and halogen, wherein halogen is preferably chlorine,
Q' and Q" together form —CH=CH— or —S—, preferably wherein when Q' and Q" together form —S—, L" is —CH$_3$,
wherein the solvent system comprises
a) 70-100% by weight of poly(ethylene glycol) with a number-average molecular weight of 1000 or less,
b) 0-30% by weight of water,
wherein the composition is a solution, and
wherein the poly(ethylene glycol) comprises less than 80 µg/g of formaldehyde impurity. Such a composition is referred to herein as a composition according to the invention.

A substance of general formula (I) is a piperazine-benzazepine, and often a piperazine-dibenzazepine. An important feature of substances of general formula (I) is that two heterocycles are fused to the azepine moiety. When Q' and Q" together form —S—, this could be seen as one of Q' and Q" being sulphur, and the other of Q' and Q" being absent. In such a case, the second heterocycle fused to the azepine moiety is an aromatic heterocycle (thiophenyl), due to lone pairs of the sulphur atom. When Q' and Q" together form —CH=CH—, this could be seen as both Q' and Q" being —CH=. In such a case, the second heterocycle fused to the azepine moiety is also an aromatic heterocycle (phenyl).

In preferred embodiments of the invention, the composition according to the invention comprises a substance of general formula (I) or a pharmaceutically acceptable salt thereof, wherein
X is —O—, —S—, or —N(H)—,
R is —H, —CH$_3$, or —(CH$_2$)$_2$—O—(CH$_2$)$_2$—OH,
L' and L" are each independently chosen from the group consisting of —H, —CH$_3$, and chlorine,
Q' and Q" together form —CH=CH— or —S—, preferably, wherein when Q' and Q" together form —S—, L" is —CH$_3$.

When X is —O—, it is preferred that Q' and Q" together form —CH=CH—. When X is —O—, it is preferred that L' is —H. When X is —O—, it is preferred that L" is —Cl. When X is —O—, it is preferred that R is —CH$_3$ or —H. Most preferably, when X is —O—, R is —CH$_3$ or —H, L' is —H, L" is —Cl, and Q' and Q" together form —CH=CH—.

When X is —S—, it is preferred that Q' and Q" together form —CH=CH—. When X is —S—, it is preferred that L' is —H. When X is —S—, it is preferred that L" is —Cl or —H. When X is —S—, it is preferred that R is —CH$_3$ or —(CH$_2$)$_2$—O—(CH$_2$)$_2$—OH. More preferably, when X is —S—, R is —CH$_3$ or —H or —(CH$_2$)$_2$—O—(CH$_2$)$_2$—OH, L' is —H, L" is —Cl or —H, and Q' and Q" together form —CH=CH—. Most preferably, when X is —S—, R is —CH$_3$ or —(CH$_2$)$_2$—O—(CH$_2$)$_2$—OH, L' is —H, L" is —Cl or —H, and Q' and Q" together form —CH=CH—.

When X is —N(H)—, it is preferred that L" is —CH$_3$ or —H, and it is more preferred that L" is —CH$_3$ when Q' and Q" together form —S—, and that L" is —H when Q' and Q" together form —CH=CH—. When X is —N(H)—, it is preferred that L' is —H or —Cl. When X is —N(H)—, it is preferred that R is —H or —CH$_3$. Most preferably, when X is —N(H)—, R is —H or —CH$_3$, L' is —Cl or —H, and L" is —CH$_3$ or —H.

In preferred compositions according to the invention, the composition comprises at least one substance of general formula (I) or a pharmaceutically acceptable salt thereof, wherein:
R is —CH$_3$, L' is —Cl, L" is —H, X is —N(H)—, and Q' and Q" together form —CH=CH—, or
R is —H, L' is —Cl, L" is —H, X is —N(H)—, and Q' and Q" together form —CH=CH—, or
R is —CH$_3$, L' is —H, L" is —CH$_3$, X is —N(H)—, and Q' and Q" together form —S—, or
R is —H, L' is —H, L" is —CH$_3$, X is —N(H)—, and Q' and Q" together form —S—, or
R is —CH$_3$, L' is —H, L" is —Cl, X is —O—, and Q' and Q" together form —CH=CH—, or
R is —H, L' is —H, L" is —Cl, X is —O—, and Q' and Q" together form —CH=CH—, or
R is —CH$_3$, L' is —H, L" is —Cl, X is —S—, and Q' and Q" together form —CH=CH—, or
R is —(CH$_2$)$_2$—O—(CH$_2$)$_2$—OH, L' is —H, L" is —H, X is —S—, and Q' and Q" together form —CH=CH—, or
R is —H, L' is —H, L" is —Cl, X is —S—, and Q' and Q" together form —CH=CH—.

Accordingly, the invention provides a composition according to the invention, wherein the substance of general formula (I) is selected from the group consisting of clozapine, norclozapine, olanzapine, norolanzapine, loxapine, amoxapine, clotiapine, quetiapine, and norquetiapine, or a pharmaceutically acceptable salt thereof, preferably clozapine or a pharmaceutically acceptable salt thereof.

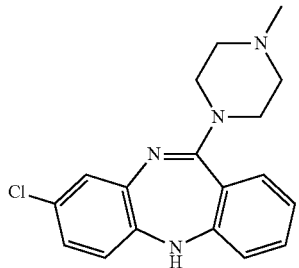

clozapine

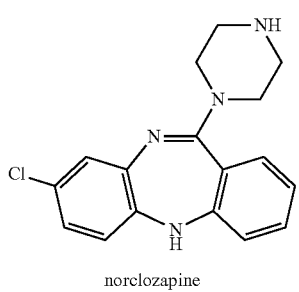

norclozapine

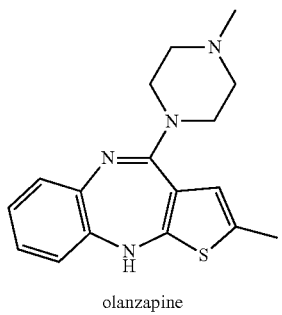

olanzapine

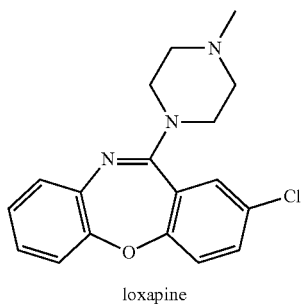

loxapine

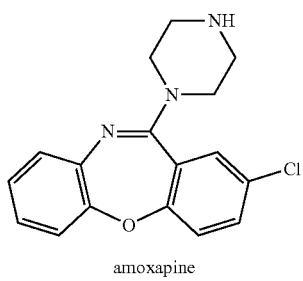

amoxapine

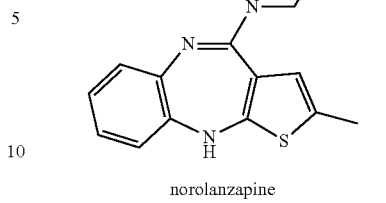

norolanzapine

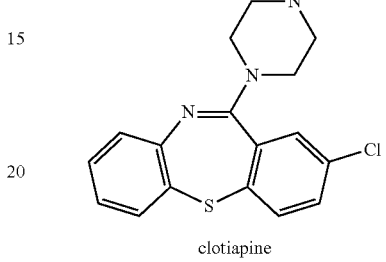

clotiapine

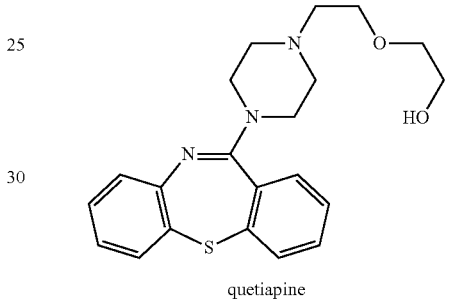

quetiapine

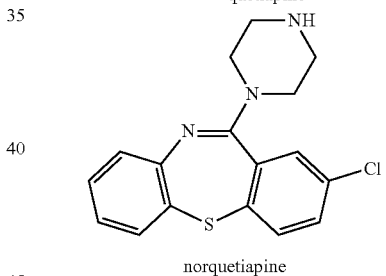

norquetiapine

Metabolites of substances of general formula (I) are also encompassed by the invention. Such metabolites can also be encompassed by general formula (I). For example, norclozapine (also known as N-desmethylclozapine, NDMC, desmethylclozapine, and 8-chloro-11-piperazin-1-yl-5H-dibenzo[b,e][1,4]diazepine) is a metabolite of clozapine (also known as clozaril and 8-Chloro-11-(4-methylpiperazin-1-yl)-5H-dibenzo[b,e][1,4]diazepine). Norolanzapine (also known as 2-Methyl-4-piperazin-1-yl-10H-thieno[2,3-13][1,5]benzodiazepine) is a metabolite of olanzapine (also known as Zyprexa and 2-Methyl-4-(4-methyl-1-piperazinyl)-10H-thieno[2,3-13][1,5]benzodiazepine). Amoxapine (also known as Asendin, Asendis, Defanyl, Demolox, and 2-chloro-11-(piperazin-1-yl)dibenzo[b,f][1,4]oxazepine) is a metabolite of loxapine (also known as adasuve, loxitane, loxapac, xylac, and 2-Chloro-11-(4-methyl-1-piperazinyl)dibenz[b,f][1,4]oxazepine). Norquetiapine (also known as 8-chloro-6-piperazin-1-yl-benzo[b][1,4]benzothiazepine) is a metabolite of quetiapine (also known as Seroquel, Temprolide, and 2-(2-(4-Dibenzo[b,f][1,4]thiazepine-11-yl-1-piperazinyl)ethoxy)ethanol) and of clotiapine (also known as Etumina, Etumine, Entumin, Etomine, Entumine, and 8-chloro-6-(4-methylpiperazin-1-yl)benzo[b][1,4]benzothiazepine.) Other metabolites are known in the art.

Preferably, compositions according to the invention comprise at least 20 mg/mL of substance of general formula (I) or a pharmaceutically acceptable salt thereof. The solvent system of the invention was surprisingly found to be suitable for the production of concentrated solutions of substances of general formula (I). In further preferred embodiments, a composition according to the invention comprises at least 5, 10, 11, 12, 13, 14, 15, 20, 25, 30, 35, 40, 45, 50, 55, 60, 65, 70, 75, 80, 85, 90, 95, 100, 105, 110, 115, 120, 125, 130, 135, 140, 145, or 150 mg/mL of substance of general formula (I) or a pharmaceutically acceptable salt thereof. Large doses of substance of general formula (I) are not always attractive as side effects may manifest more clearly. Precise dosing also helps in personalized medicine for treatments with a particular pharmacogenetic profile. Therefore, in more preferred embodiments, this aspect provides a composition according to the invention, comprising at least 11 mg/mL, preferably at least 50 mg/mL, more preferably at least 70 mg/mL of a substance of general formula (I) or a pharmaceutically acceptable salt thereof. Preferably, a composition according to the invention comprises no more than 150, 110, 100, 90, 80, 70, 60, or 50 mg/mL of a substance of general formula (I) or a pharmaceutically acceptable salt thereof. When more than one substance of general formula (I) or a pharmaceutically acceptable salt thereof is present in a composition according to the invention, the cumulative weight is intended, that is the sum of the weights of individual substances of general formula (I) or their pharmaceutically acceptable salts is intended. In preferred embodiments, the compositions comprise only a single substance of general formula (I) or a pharmaceutically acceptable salt thereof. In other preferred embodiments, the compositions comprise more than one substance of general formula (I) or pharmaceutically acceptable salts thereof. When more than one substance of general formula (I) or a pharmaceutically acceptable salt thereof is comprised in a composition, it is preferred that clozapine or a pharmaceutically acceptable salt thereof is at least comprised in said composition. The amounts described above are preferably for free base substances of general formula (I), not for salts. For compositions comprising a pharmaceutically acceptable salt of a substance of formula (I), the amounts described above preferably relate to the actual content of substance of general formula (I), or in other words the counter ion of the substance of general formula (I) is preferably not counted towards the limits described above.

Compositions according to the invention comprise a solvent system. Generally, a solvent system is a mixture of one or more solvents, although individual solvents can also constitute a solvent system depending on context. For example, when a solvent system is described in percentage ranges for various components, and the range of a component encompasses either 0% or 100%, the resulting solvent system might in fact be comprised of a single remaining solvent.

Solvent systems according to the invention comprise short poly(ethylene glycol). Poly(ethylene glycol) is a polymer also known as PEG, poly(ethylene oxide), poly(oxyethylene), and macrogol, amongst others. It is generally tasteless, odourless, and colourless. Due to their generally short chain length, short PEGs are sometimes referred to as oligo(ethylene glycol)s. It consists of repeating monomers (—CH2-CH2-O—) and the termini most often feature hydroxyl groups, sometimes capped as methyl ether or as another chemically and pharmacologically inert moiety. Preferably, PEGs for use in the invention have hydroxyl termini. Preferred PEGs are selected from the group consisting of $PEG_3$, $PEG_4$, $PEG_5$, $PEG_6$, $PEG_7$, $PEG_8$, $PEG_{10}$, $PEG_{11}$, $PEG_{12}$, $PEG_{13}$, $PEG_{14}$, $PEG_{15}$, $PEG_{16}$, $PEG_{17}$, $PEG_{18}$, $PEG_{19}$, $PEG_{20}$, $PEG_{21}$, $PEG_{22}$, and $PEG_{23}$, wherein the subscript denotes the average number of repeating monomers (—CH2-CH2-O—) present in the PEG chain. Polymers are often polydisperse, and therefore PEG is also commonly denoted by mentioning its average molecular weight, rounded to a near round number. For example, PEG3000 generally refers to the same polymer as at least $PEG_{65}$ and $PEG_{68}$. PEG2000 generally refers to the same polymer as at least $PEG_{44}$ and $PEG_{48}$. PEG500 generally refers to the same polymer as at least $PEG_{10}$, $PEG_{11}$, and $PEG_{12}$. The preceding does not hold when context makes it specific that a discrete PEG is referenced, consisting of a fixed amount of monomers. Preferred poly(ethylene glycol)s with a number-average molecular weight of 1000 or less are selected from the group comprising PEG100 to PEG1000, more particularly from the group consisting of PEG150, PEG200, PEG250, PEG300, PEG350, PEG400, PEG450, PEG500, PEG550, PEG600, PEG700, PEG800, PEG900, and PEG1000. More preferred poly(ethylene glycol)s with a number-average molecular weight of 1000 or less are PEG300, PEG400, PEG500, and PEG600. Other more preferred poly(ethylene glycol)s with a number-average molecular weight of 1000 or less are PEG400, PEG500, and PEG600. These short PEGs are attractive because they are well-manageable liquids which were surprisingly found to be good solvents for substances of general formula (I) or their pharmaceutically acceptable salts, forming stable solutions. Most preferred poly(ethylene glycol)s with a number-average molecular weight of 1000 or less are PEG400 and PEG600. PEG400 is a highly preferred poly(ethylene glycol) with a number-average molecular weight of 1000 or less. PEG600 is a highly preferred poly(ethylene glycol) with a number-average molecular weight of 1000 or less. Accordingly, preferred embodiments of this aspect provide a composition according to the invention, wherein the poly (ethylene glycol) has a number-average molecular weight of 200-800, preferably of 200-700, more preferably of 200-600. In other preferred embodiments, the poly(ethylene glycol) has a number-average molecular weight of 300-700 or of 300-600.

Short poly(ethylene glycol)s as defined herein are poly (ethylene glycol)s with a number-average molecular weight of 1000 or less. Preferably, short poly(ethylene glycol) with a number-average molecular weight of 1000 or less have a number-average molecular weight of 200 or more. As a skilled person will understand, ethylene glycol and diethylene glycol are not suitable for use in the invention. As such, preferred embodiments of the invention provide the use of poly(ethylene glycol) with a number-average molecular weight of 200 to 1000. These PEGs are generally liquid at ambient conditions. Those that are not, generally become liquid upon admixture of up to 30% by weight of water. Therefore, the solvent system according to the invention comprises:

a) 70-100% by weight of poly(ethylene glycol) with a number-average molecular weight of 1000 or less,
b) 0-30% by weight of water. As such, a solvent system according to the invention can consist of 100% PEG. Preferably, water is purified or highly purified water, such as distilled water, double-distilled water, deionized water, or ultrapure water. A skilled person can select water suitable for use as an excipient. The pH of the water component of the solvent system is preferably at least 4.5, 5.0, 5.5, 6.0, 6.5, 7.0, 7.5, 8.0, 8.5, or 9.0. It is most preferred that the pH of the water component is at least 5.0, 5.5, 6.0, 6.5, 7.0, or 7.5. In general, pH values below 4.0 decrease the stability of the composition according to the invention.

Preferred solvent systems according to the invention comprise 70-100% by weight of poly(ethylene glycol) with a number-average molecular weight of 200 to 1000, and b) 0-30% by weight of water. More preferred solvent systems according to the invention comprise 70-100% by weight of poly(ethylene glycol) with a number-average molecular weight of 200 to 800, and b) 0-30% by weight of water. Even more preferred solvent systems according to the invention comprise 70-100% by weight of poly(ethylene glycol) with a number-average molecular weight of 300 to 700, and b) 0-30% by weight of water. The most preferred solvent systems according to the invention comprise 70-100% by weight of poly(ethylene glycol) with a number-average molecular weight of 200 to 600, and b) 0-30% by weight of water.

In highly preferred embodiments, no other solvents are present. This facilitates formulation, and avoids possible undesirable solvent effects. Undesirable solvent effects can be the administration of an alcohol such as ethanol to subjects who may have a history of substance abuse, or the administration of an alcohol such as benzyl alcohol to an allergic subject, triggering anaphylaxis. Possible hydroxyl moieties of the PEG are not relevant in this context, as they are not comprised in a sufficiently small organic molecule. Therefore, preferred solvent systems or compositions according to the invention do not comprise ethanol and/or do not comprise benzyl alcohol and/or do not comprise propylene glycol. More preferred solvent systems or compositions according to the invention do not comprise ethanol and do not comprise benzyl alcohol. Even More preferred solvent systems or compositions according to the invention do not comprise benzyl alcohol and propylene glycol. Most preferred solvent systems or compositions according to the invention do not comprise ethanol, benzyl alcohol, and propylene glycol. Preferred solvent systems according to the invention consist of 70-100% by weight of poly(ethylene glycol) with a number-average molecular weight of 200 to 1000, and b) 0-30% by weight of water. More preferred solvent systems according to the invention consist of 70-100% by weight of poly(ethylene glycol) with a number-average molecular weight of 200 to 800, and b) 0-30% by weight of water. Even more preferred solvent systems according to the invention consist of 70-100% by weight of poly(ethylene glycol) with a number-average molecular weight of 300 to 700, and b) 0-30% by weight of water. Most highly preferred solvent systems according to the invention consist of 70-100% by weight of poly(ethylene glycol) with a number-average molecular weight of 200 to 600, and b) 0-30% by weight of water.

The ability of PEGs to form complexes with active substances can be responsible for their excellent solvent properties. However, equilibrium constants for complex formation vary considerably from one solute to another, and examples are known of hydrophobic drugs being inactivated due to PEG complexation. This is known for poorly soluble drugs, such as for example penicillin V (David H. Sieh, in "Analytical profiles of drug substances" (Vol 17, editor: Klaus Florey) 1988) page 696) and phenobarbital, an agent for treatment of seizures (Sarfaraz K. Niazi, in "Handbook of bioequivalence testing", 2007, $1^{st}$ edition, table 12, page 180).

The composition according to the invention is a solution. A solution is a mixture composed of two or more substances, at least comprising a solute, which is a substance that is dissolved, dissolved in another substance, this other substance being referred to as a solvent. A solution is preferably homogeneous. Compositions according to the invention use a solvent system as described above as a solvent, and use a substance of general formula (I) or a pharmaceutically acceptable salt thereof as a solute. A solution preferably has no suspended solid particles, and preferably has no emulsified liquid phase. This reduces risk associated with clogging when a solution is for injection. This reduces risk of incomplete administration due to precipitation or caking when a solution is for oral administration. Compared to suspensions or emulsions, solutions can be more readily assayed for purity, stability, or possible contaminants, as no treatment is required to enable assay conditions. The adsorption and distribution of a solute is generally higher than that of a solid. It is envisaged that solutions according to the invention can be used as liquid phase for the preparation of further suspensions or emulsions. A skilled person will know how to do this.

Compositions according to the invention have very low levels of formaldehyde impurity, namely less than 80 µg/g. While formaldehyde is not an intentional component of the compositions, formaldehyde is a common residual impurity in many solvents and excipients such as polysorbate, povidone, and poly(ethylene glycol). The presence of this impurity can potentially decrease the stability of drug substances by reacting with amino groups. Formaldehyde is also susceptible to oxidation and is partially converted to formic acid on contact with air (Del Barrio et al., J. Pharm. Biomed. Anal. (2005) doi:10.1016/j.jpba.2005.12.033). Formaldehyde is particularly common in short PEGs, and can be generated from the solvent itself, reaching concentrations of 2400 ppm (Frontini and Mielck, In. J. Pharm. (1995) 114: 121-123—ppm equates µg/g in this context). Other aldehydes, such as acetaldehyde, are less common and exist in concentrations of at most about 5% of formaldehyde levels. Even pharmaceutical grade PEGs can still contain high aldehyde levels of over 900 ppm (for PEG600) or almost 200 ppm (for PEG400). (Li et al., J. Chromatogr. A (2006) doi:10.1016/j.chroma.2005.10.084) or more than 85 ppm (for PEG400, Del Barrio 2005). Del Barrio also reports a formic acid level of more than 450 ppm, and teaches the conversion of formaldehyde to formic acid, suggesting higher initial formaldehyde levels. Li et al. also reports that formaldehyde levels drop to almost zero for PEG1450 and PEG4000, but these poly(ethylene glycol)s are too long to be suitable for use in the invention.

In preferred embodiments of this aspect, the poly(ethylene glycol) comprises less than 70, 65, 60, 55, 50, 45, 40,35, 30, 25, 20, or 15 µg/g of formaldehyde impurity. In more preferred embodiments, this aspect provides the composition according to the invention, wherein the poly(ethylene glycol) comprises less than 50 µg/g of formaldehyde impurity. In even more preferred embodiments, this aspect provides the composition according to the invention, wherein the poly(ethylene glycol) comprises less than 30 µg/g of formaldehyde impurity. In most preferred embodiments, this aspect provides the composition according to the invention, wherein the poly(ethylene glycol) comprises less than 15 µg/g of formaldehyde impurity.

Aldehyde impurity levels can be assessed using headspace chromatographic techniques, for example after derivatization of aldehydes in aqueous solution with O-2,3,4,5,6-(pentafluorobenzyl) hydroxylamine hydrochloride (PFBHA), followed by static headspace gas chromatographic (SHS-GC) analysis of PFBHA aldehyde oximes with negative chemical ionization (NCI) MS detection (see Li et al.) or via a one-step procedure requiring dissolving or dispersion of samples in acidified ethanol reagent to convert formaldehyde to diethoxymethane, followed by GC/MS analysis (see Del Barrio et al.).

In preferred embodiments of this aspect, the poly(ethylene glycol) further has a pH value (5%; water, 25° C.) of 4 to 7, a kinematic viscosity (20° C.) of 100-111 mm$^2$/s for PEG400, or 14.8-17.6 mm$^2$/s for PEG600, contains at most 20 ppm trace heavy metals, and at most 0.4% by weight of ethylene glycol and diethylene glycol, preferably at most 0.25% for PEG400. A preferred hydroxyl value is 264-300 for PEG400, or 178-197 for PEG600, and a preferred average molecular mass deviates about 5% from the number average molecular weight. It is preferred to use poly(ethylene glycol) with a peroxide content of at most 100 ppm, and a dioxane content of at most 10 ppm.

It is preferred that the compositions according to the invention are not overly viscous, to enable facile handling of the solution. Therefore, in preferred embodiments, the composition according to the invention has a viscosity at 25° C. of no more than 2000 cP, preferably no more than 1000 cP, more preferably no more than 500 cP, most preferably no more than 250 cP. In other preferred embodiments, the composition according to the invention has a viscosity at 25° C. of no more than 200 or 180 cP. A preferred method for determining viscosity is by use of a HAAKE Viscometer C at 25° C. and 200 RPM.

There is no need to deaerate the poly(ethylene glycol), nor to sparge it with an inert gas, or to purge oxygen in any way. In preferred embodiments, the poly(ethylene glycol) has not been treated to remove oxygen. PEG 400 contains about 2-4 mg/L molecular oxygen in compositions comprising 70-100% PEG400 and 0-30% water (Guilminot et al., Corrosion Science (2002) 44: 2199-2208). As a result, in preferred embodiments is provided a composition comprising a solvent system and a substance of general formula (I) or a pharmaceutically acceptable salt thereof, wherein the solvent system comprises a) 70-100% by weight of poly(ethylene glycol) with a number-average molecular weight of 1000 or less, b) 0-30% by weight of water, wherein the composition is a solution, and wherein the poly(ethylene glycol) comprises less than 80 μg/g of formaldehyde impurity and wherein the composition comprises at least 1.1 mg/L molecular oxygen, preferably at least 1.5 mg/L molecular oxygen, most preferably at least 2 mg/L molecular oxygen. In most preferred embodiments, this aspect provides a composition comprising a solvent system and a substance of general formula (I) or a pharmaceutically acceptable salt thereof, wherein the solvent system comprises a) 70-100% by weight of poly(ethylene glycol) with a number-average molecular weight of 1000 or less, b) 0-30% by weight of water, wherein the composition is a solution, and wherein the poly(ethylene glycol) comprises less than 80 μg/g of formaldehyde impurity and wherein the composition comprises about 2-4 mg/L molecular oxygen.

The compositions according to the invention are very stable. This means that the substance of general formula (I) does not precipitate or degrade to a relevant degree, and that degradation products of substances of general formula (I) do not appear over time. As shown in the examples, the solutions maintain a consistently high level of active ingredient, while impurities such as N-oxides do not form to a relevant degree.

Thus, in preferred embodiments of this aspect is provided the composition according to the invention, wherein the substance of general formula (I) or the pharmaceutically acceptable salt thereof is stable for at least one month, preferably for at least six months. In this context, a substance of general formula (I) can be said to be stable if at least 95% of it can be assayed after at least 6 months, or if at least 98.5% of it can be assayed after at least 1 month. Another measure for stability is the formation of impurities that are degradation products of the substance of general formula (I). A solution can be said to be stable if less than 1% impurities can be assayed after at least 6 months. Analytical HPLC methods are preferred to assay active ingredients or impurities, preferably HPLC methods as described in the examples. Therefore, in preferred embodiments of this aspect is provided the composition according to the invention, wherein the substance of general formula (I) or the pharmaceutically acceptable salt thereof is still present at at least 95%, preferably 96%, more preferably 97%, most preferably 98%, 99%, or 99.5% of its original concentration after at least one month, preferably after at least six months. Similarly, in preferred embodiments of this aspect is provided the composition according to the invention, wherein degradation products of the substance of general formula (I) or the pharmaceutically acceptable salt thereof are present at at most 1%, preferably 0.8%, more preferably 0.6%, most preferably 0.5%, 0.4%, 0.3%, or 0.2% after at least one month, preferably after at least six months. In this context, percentages are expressed as mole percentages of total concentration of impurities plus active ingredient.

The stability of the compositions according to the invention can be further enhanced through the addition of antioxidants. Antioxidants inhibit the oxidation of other molecules and thus help prevent aldehyde formation in compositions of the invention. Examples of antioxidants are ascorbic acid, tocopherols, methionine (preferably L-methionine), metabisulphite, propyl gallate, butylated hydroxyanasole, butylated hydroxytoluene, meglumine, and thiosulphate salts; preferred antioxidants are ascorbic acid, tocopherols, methionine (preferably L-methionine), metabisulphite, propyl gallate, butylated hydroxyanasole, butylated hydroxytoluene, meglumine, and thiosulphate salts. More preferred antioxidants are propyl gallate, thiosulphate salts, preferably sodium thiosulphate, and tocopherols, preferably α-tocopherols, more preferably α-tocopherol-PEG-succinate. A-tocopherol-PEG-succinate is a commercially available conjugate of α-tocopherol with PEG1000, and has high solubility in short PEGs. Most preferred antioxidants are thiosulphate salts, preferably sodium thiosulphate, and tocopherols, preferably α-tocopherols, more preferably α-tocopherol-PEG-succinate. In preferred embodiments is provided the composition according to the invention, further comprising an antioxidant such as a thiosulphate salt, propyl gallate, or a tocopherol. In more preferred embodiments is provided the composition according to the invention, further comprising an antioxidant selected from thiosulphate salt and/or a tocopherol. In most preferred embodiments is provided the composition according to the invention, further comprising an antioxidant selected from sodium thiosulphate and/or an α-tocopherol, preferably α-tocopherol-PEG-succinate.

For some applications, it is preferred that the concentration of substance of general formula (I) or its pharmaceutically acceptable salt is relatively high. For example, when capsules are filled with the solution of the invention, it is preferred that these capsules have a volume that can still be conveniently swallowed by patients, promoting patient compliance. A high concentration of active ingredient enables capsule volume to remain low. It was found that nonioinic surfactants, when present in the composition according to the invention, can increase the solubility of the substance of general formula (I) or its pharmaceutically acceptable salt. Examples of nonionic surfactants are poly(ethylene glycol)$_{15}$-hydroxystearate, oligo(ethylene glycol) monoethyl ethers such as diethylene glycol monoethyl ether or triethylene glycol monoethyl ether, glycerol monolaurate, polysorbate, polyoxyl 40 hydrogenated castor oil (also known as macrogolglycerol hydroxystearate), and polyethylene glycol (15)-hydroxystearate (also known as Macrogol (15)-hydroxystearate, Kolliphor HS15, and Solutol HS 15). Excellent solubility was achieved upon addition of oligo(ethylene glycol) monoethyl ethers such as Transcutol P (diethylene glycol monoethyl ether). Therefore, preferred embodiments provide the composition according to the invention, further comprising a nonionic surfactant, preferably an oligo(ethylene glycol) monoethyl ether, more preferably diethylene glycol monoethyl ether. It is preferred that the composition according to the invention comprises no more than 50% by weight of the nonionic surfactant. More preferably, the composition according to the invention comprises no more than 20% by weight of a nonionic surfactant. Even more preferably, the composition according to the invention comprises no more than 10% by weight of a nonionic surfactant. Most preferably, the composition according to the invention comprises no more than 5% by weight of a nonionic surfactant.

Patient compliance can also be increased by making the composition according to the invention more attractive to the senses of a subject. Piperazine-benzazepines generally have a rather bitter taste. Therefore, different flavouring agents, acids, sweeteners, and oils can be added to the formulation to mask the taste. Examples of suitable flavouring agents are citric acid, menthol, limonene (either enantiomer), and peppermint oil. Examples of suitable sweetening agents are aspartame, acesulfam K, and sucralose. A skilled person will know how to dose flavouring agents and sweetening agents. Generally, low amounts are required, such as at most 10 mg/mL, at most 7.5 mg/mL, at most 5 mg/mL, at most 4 mg/mL, at most 3 mg/mL, at most 2 mg/mL, or at most 1 mg/mL. As such, preferred embodiments provide the composition according to the invention, further comprising at most 10 mg/mL by weight of flavouring or sweetening agents such as sucralose or peppermint oil, preferably at most 2 mg/mL by weight.

The compositions according to the invention are easy to prepare due to their elegant formulation. Low complexity also promotes stability by avoiding undesired interactions between substances. In preferred embodiments, the compositions according to the invention essentially consist of
 i) a substance of general formula (I) or a pharmaceutically acceptable salt thereof, and
 ii) a solvent system consisting essentially of 70-100% by weight poly(ethylene glycol) with a number-average molecular weight of 1000 or less and 0-30% by weight of water.
In other preferred embodiments, the compositions according to the invention essentially consist of
 i) a substance of general formula (I) or a pharmaceutically acceptable salt thereof, and
 ii) a solvent system consisting essentially of 70-100% by weight poly(ethylene glycol) with a number-average molecular weight of 1000 or less and 0-30% by weight of water, and
 iii) optionally one or more flavouring or sweetening agent, and
 iv) optionally one or more antioxidant.

In this context, "to consist essentially of" is to be interpreted as not intentionally comprising other components, or comprising at most 2% by weight of other components, preferably at most 1% by weight of other components, more preferably at most 0.1% by weight of other components, most preferably at most 0.01% by weight of other components.

Compositions according to the invention are advantageous for use as a medicament. Therefore, compositions according to the invention are preferably pharmaceutical compositions, preferably formulated:
 i) as an injectable preparation, either for subcutaneous, intravenous, or intramuscular administration, or
 ii) as a solution for oral administration, or
 iii) as a liquid-filled capsule, preferably a softgel capsule.

The composition according to the invention may be formulated for parenteral administration by injection, e.g., by bolus injection or continuous infusion. Formulations for infection may be presented in unit dosage form, e.g., in ampoules or in multi-dose container, with an added preservative such as an antioxidant defined earlier herein.

Pharmaceutical compositions which can be administered orally include push-fit capsules made of gelatin, as well as soft, sealed capsules made of gelatin and a plasticizer, such as glycerol or sorbitol. These capsules are referred to as softgel capsules. Stabilizers may be added. All formulations for oral administration are preferably in dosages suitable for such administration.

Generally speaking, such types of formulation are known in the art, and a skilled person will be able to use the composition according to the invention to obtain such formulations.

Use

In another aspect of the invention, the compositions as defined above are for use as a medicament. Accordingly, this aspect provides the composition according to the invention, for use as a medicament, preferably for treatment of psychosis. Psychosis is an abnormal condition of the mind. Subjects suffering from psychosis may exhibit personality changes and thought disorder. Depending on its severity, this may be accompanied by unusual or bizarre behavior, as well as difficulty with social interaction and impairment in carrying out daily life activities. The first-line treatment for many psychotic disorders is antipsychotic medication. Piperazine-benzazepines such as clozapine are known as atypical antipsychotic medication. They are mainly used for treatment of more severe forms of psychosis, such as schizophrenia that does not improve following the use of other antipsychotic medications. In subjects suffering from schizophrenia and schizoaffective disorder, piperazine-benzazepines may decrease the rate of suicidal behavior.

A compound for use is preferably for the treatment, amelioration, delay, cure, or stabilization of psychosis, preferably in a subject in need thereof. The use preferably comprises administration of an effective dose of a composition for use according to the invention to a subject in need thereof. Preferably, this aspect provides the composition according to the invention, for treatment of psychosis, wherein psychosis is preferably schizophrenia or psychosis caused by Parkinson's disease.

Within this aspect, preferred embodiments provide the composition for use according to the invention, wherein the composition is for oral administration, preferably in a daily dose of at least 6 mg. For treatment of psychosis associated with Parkinson's disease, doses of 6.25 to 12.5 mg per day are suitable. For treatment of other forms of psychosis, doses of 400 mg per day are suitable. For severe psychosis, doses of 1000-1200 mg per day are suitable. In preferred embodiments, the composition for use according to the invention is for administration in a daily dose of at least 6 mg and at most 1200 mg. In preferred embodiments, the composition for use according to the invention is for treatment of psychosis associated with Parkinson's disease, and is for administration in a daily dose of about 6.25 mg to about 12.5 mg. In preferred embodiments, the composition for use according to the invention is for treatment of psychosis not associated with Parkinson's disease and is for administration in a daily dose of at least about 400 mg and at most about 1200 mg. In preferred embodiments, the composition for use according to the invention is for treatment of severe psychosis and is for administration in a daily dose of at least about 1000 mg and at most about 1200 mg. In preferred embodiments, the composition for use according to the invention is for treatment of non-severe psychosis and is for administration in a daily dose of at least about 300 mg and at most about 500 mg.

Within this aspect, preferred embodiments provide the composition for use according to the invention, wherein the composition is for administration at least one time per day. Preferred administration is a regime comprising two doses, a so-called morning dose and a so-called evening dose. Accordingly, preferred embodiments provide the composition for use according to the invention, wherein the composition is for administration at least two times per day. Generally, an evening dose comprises more substance of general formula (I) or a pharmaceutically acceptable salt thereof than a morning dose. Further preferred embodiments provide the composition for use according to the invention, wherein the use is for treatment of psychosis not associated with Parkinson's diseases, and the composition is for administration two times per day. Further preferred embodiments provide the composition for use according to the invention, wherein the use is for treatment of psychosis associated with Parkinson's diseases, and the composition is for administration one time per day.

Suitable methods of administration have already been described above. Suitable doses have also been described herein. The amount of composition administered will, of course, be dependent on the subject being treated, on the subject's weight, the severity of the affliction, the manner of administration, and the judgment of the prescribing physician.

Method of Treatment

In another aspect of the invention, a method of treatment is provided. Preferably, the method is a method of treating, ameliorating, delaying, curing, or stabilizing psychosis, said method comprising the step of administering to a subject in need thereof an effective dose of a composition according to the invention. The method comprises administering to a subject a composition according to the invention. Preferably, the method comprises administering to a subject in need thereof an effective dose of a composition according to the invention. The method preferably comprises the use of a composition as described earlier herein.

Method of Preparation

In another aspect of the invention, a method for preparing compositions according to the invention is provided. Preferably, the method is a method of preparing a composition according to the invention, comprising the steps of:
i) providing a substance of general formula (I) in a suitable container,
ii) adding a solvent system according to the invention,
iii) stirring the solution.

Preferably, stirring in step iii) is for at least two hours. A preferred method of stirring is by use of an upper stirrer, preferably at 500 rpm. Stirring is preferably continued until a clear solution is obtained. In preferred embodiments is provided a method of preparing a composition according to the invention, comprising the steps of:
i) providing a substance of general formula (I) in a suitable container,
ii) adding a solvent system according to the invention,
iii) stirring the solution until a clear solution is obtained,
iv) adding flavouring and/or sweetening agent,
v) stirring the solution until a clear solution is obtained.

In preferred embodiments is provided a method of preparing a composition according to the invention, comprising the steps of:
i) providing a substance of general formula (I) in a suitable container,
ii) adding an amount of a solvent system according to the invention to obtain about a 50 mg/mL solution of substance of general formula (I),
iii) stirring the solution for at least two hours,
iv) an amount of at least one flavouring and/or sweetening agent to obtain a final concentration of about 0.1% by weight, and
v) stirring the solution for at least two hours.

The invention has been described above with reference to a number of exemplary embodiments. Modifications and alternative implementations of some parts or elements are possible, and are included in the scope of protection as defined in the appended claims.

Particular Embodiments

1. The composition according to the invention, wherein the composition comprises:
   i) a substance of general formula (I) or a pharmaceutically acceptable salt thereof, and
   ii) a solvent system comprising 70-100% by weight poly(ethylene glycol) with a number-average molecular weight of 1000 or less and 0-30% by weight of water, and
   iii) optionally one or more flavouring or sweetening agent, and
   iv) optionally one or more antioxidant.
2. The composition according to the invention, wherein the composition comprises:
   i) clozapine, norclozapine, olanzapine, norolanzapine, loxapine, amoxapine, clotiapine, quetiapine, and/or norquetiapine, and/or any pharmaceutically acceptable salt thereof, preferably clozapine or a pharmaceutically acceptable salt thereof, and
   ii) a solvent system comprising 70-100% by weight poly(ethylene glycol) with a number-average molecular weight of 1000 or less and 0-30% by weight of water, and
   iii) optionally one or more flavouring or sweetening agent, and
   iv) optionally one or more antioxidant.
3. The composition according to the invention, wherein the composition consists of:
   i) a substance of general formula (I) or a pharmaceutically acceptable salt thereof, preferably clozapine or a pharmaceutically acceptable salt thereof, and ii) a solvent system consisting essentially of 70-100% by weight poly(ethylene glycol) with a number-average molecular weight of 1000 or less and 0-30% by weight of water, and
iii) optionally one or more flavouring or sweetening agent, and
iv) optionally one or more antioxidant.
4. The composition according to the invention, wherein the composition consists of:
i) clozapine, norclozapine, olanzapine, norolanzapine, loxapine, amoxapine, clotiapine, quetiapine, and/or norquetiapine, and/or any pharmaceutically acceptable salt thereof, preferably clozapine or a pharmaceutically acceptable salt thereof, and
ii) a solvent system consisting essentially of 70-100% by weight poly(ethylene glycol) with a number-average molecular weight of 1000 or less and 0-30% by weight of water, and
iii) optionally one or more flavouring or sweetening agent, and
iv) optionally one or more antioxidant.
5. The composition according to embodiment 1, comprising a total of at most 0.5% by weight, preferably at most 0.1% by weight of flavouring and/or sweetening agent, preferably sucralose and/or peppermint oil.
6. The composition according to embodiment 2, comprising a total of at most 0.5% by weight, preferably at most 0.1% by weight of flavouring and/or sweetening agent, preferably sucralose and/or peppermint oil.
7. The composition according to embodiment 3, comprising a total of at most 0.5% by weight, preferably at most 0.1% by weight of flavouring and/or sweetening agent, preferably sucralose and/or peppermint oil.
8. The composition according to embodiment 4, comprising a total of at most 0.5% by weight, preferably at most 0.1% by weight of flavouring and/or sweetening agent, preferably sucralose and/or peppermint oil.
9. The composition according to embodiment 1 or 5, comprising at most 1% by weight, preferably at most 0.5% by weight of antioxidant.
10. The composition according to embodiment 2 or 6, comprising at most 1% by weight, preferably at most 0.5% by weight of antioxidant.
11. The composition according to embodiment 3 or 7, comprising at most 1% by weight, preferably at most 0.5% by weight of antioxidant.
12. The composition according to embodiment 4 or 8, comprising at most 1% by weight, preferably at most 0.5% by weight of antioxidant.
13. The composition according to any of embodiments 9-12, wherein the antioxidant is a thiosulphate salt, a tocopherol, and/or propyl gallate.
14. The composition according to any of embodiments 9-12, wherein the antioxidant is sodium thiosulphate, α-tocopherol, and/or propyl gallate.
15. The composition according to any of embodiments 9-12, wherein the antioxidant is sodium thiosulphate and/or α-tocopherol-PEG-succinate.
16. The composition according to any of embodiments 1-15, wherein the solvent system comprises 80-100% by weight poly(ethylene glycol) with a number-average molecular weight of 1000 or less and 0-20% by weight of water.
17. The composition according to any of embodiments 1-15, wherein the solvent system comprises 85-100% by weight poly(ethylene glycol) with a number-average molecular weight of 1000 or less and 0-15% by weight of water.
18. The composition according to any of embodiments 1-15, wherein the solvent system comprises 88-100% by weight poly(ethylene glycol) with a number-average molecular weight of 1000 or less and 0-12% by weight of water.
19. The composition according to any of embodiments 1-15, wherein the solvent system comprises 90-100% by weight poly(ethylene glycol) with a number-average molecular weight of 1000 or less and 0-10% by weight of water.
20. The composition according to any of embodiments 1-15, wherein the solvent system comprises 95-100% by weight poly(ethylene glycol) with a number-average molecular weight of 1000 or less and 0-5% by weight of water.
21. The composition according to any of embodiments 1-15, wherein the solvent system comprises 100% by weight poly(ethylene glycol) with a number-average molecular weight of 1000 or less.
22. The composition according to any of embodiments 1-21, wherein the poly(ethylene glycol) has a number-average molecular weight of 200-1000.
23. The composition according to any of embodiments 1-21, wherein the poly(ethylene glycol) has a number-average molecular weight of 200-1000.
24. The composition according to any of embodiments 1-21, wherein the poly(ethylene glycol) has a number-average molecular weight of 200-800.
25. The composition according to any of embodiments 1-21, wherein the poly(ethylene glycol) has a number-average molecular weight of 200-700.
26. The composition according to any of embodiments 1-21, wherein the poly(ethylene glycol) has a number-average molecular weight of 200-600.
27. The composition according to any of embodiments 1-21, wherein the poly(ethylene glycol) has a number-average molecular weight of 300-700.
28. The composition according to any of embodiments 1-21, wherein the poly(ethylene glycol) has a number-average molecular weight of 300-600.
29. The composition according to any of embodiments 1-21, wherein the poly(ethylene glycol) has a number-average molecular weight of 400-600.
30. The composition according to any of embodiments 1-21, wherein the poly(ethylene glycol) has a number-average molecular weight of 400.
31. The composition according to any of embodiments 1-21, wherein the poly(ethylene glycol) has a number-average molecular weight of 600.
32. The composition according to embodiment 1, consisting of clozapine or a pharmaceutically acceptable salt thereof, dissolved in PEG400.
33. The composition according to embodiment 1, consisting of clozapine or a pharmaceutically acceptable salt thereof, and a tocopherol, preferably α-tocopherol-PEG-succinate, dissolved in PEG400.
34. The composition according to embodiment 1, consisting of clozapine or a pharmaceutically acceptable salt thereof, dissolved in a solvent system consisting of 90% by weight of PEG400 and 10% by weight of water.
35. The composition according to embodiment 1, consisting of clozapine or a pharmaceutically acceptable salt thereof, and at most 1% by weight of a thiosulphate salt, preferably sodium thiosulphate, and at most 1% by weight of a tocopherol, preferably α-tocopherol-PEG-succinate, dissolved in a solvent system consisting of 90% by weight of PEG400 and 10% by weight of water.
36. The composition according to embodiment 1, consisting of clozapine or a pharmaceutically acceptable salt thereof, dissolved in a solvent system consisting of 90% by weight of PEG600 and 10% by weight of water.

37. The composition according to embodiment 1, consisting of clozapine or a pharmaceutically acceptable salt thereof, and at most 1% by weight of a thiosulphate salt, preferably sodium thiosulphate, and at most 1% by weight of a tocopherol, preferably α-tocopherol-PEG-succinate, dissolved in a solvent system consisting of 90% by weight of PEG600 and 10% by weight of water.

38. The composition according to embodiment 1, consisting of clozapine or a pharmaceutically acceptable salt thereof, and at most 0.5% by weight of sucralose and/or peppermint oil, dissolved in PEG400.

39. The composition according to embodiment 1, consisting of clozapine or a pharmaceutically acceptable salt thereof, and a tocopherol, preferably α-tocopherol-PEG-succinate, and at most 0.5% by weight of sucralose and/or peppermint oil, dissolved in PEG400.

40. The composition according to embodiment 1 or 2, comprising at most 20% diethylene glycol monoethyl ether.

41. The composition according to embodiment 1, consisting of clozapine or a pharmaceutically acceptable salt thereof, and at most 1% by weight of a thiosulphate salt, preferably sodium thiosulphate, and at most 1% by weight of a tocopherol, preferably α-tocopherol-PEG-succinate, dissolved in a solvent system consisting of 88% by weight of PEG400, 10% by weight of water, and 2% by weight of diethylene glycol monoethyl ether.

42. The composition according to embodiment 1, consisting of clozapine or a pharmaceutically acceptable salt thereof, and at most 1% by weight of a thiosulphate salt, preferably sodium thiosulphate, and at most 1% by weight of a tocopherol, preferably α-tocopherol-PEG-succinate, dissolved in a solvent system consisting of 88% by weight of PEG600, 10% by weight of water, and 2% by weight of diethylene glycol monoethyl ether.

43. The composition according to any of embodiment 1-42, comprising at least 30 mg/mL, preferably at least 50 mg/mL, more preferably at least 70 mg/mL of the substance of general formula (I) or a pharmaceutically acceptable salt thereof.

44. The composition according to any of embodiment 1-43, wherein the poly(ethylene glycol) comprises less than 30 μg/g of formaldehyde impurity.

45. The composition according to any of embodiments 1-44, having a viscosity at 25° C. of no more than 2000 cP, preferably no more than 1000 cP, more preferably no more than 500 cP, most preferably no more than 250 cP General Definitions In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Pharmaceutically acceptable salts are known in the art. A skilled person can determine which salts are acceptable. See for example Stahl & Wermuth, ed. "Pharmaceutical Salts: Properties, Selection, and Use" Wiley & sons, 2002, ISBN-13 978-3-90639026-0

Each embodiment as identified herein may be combined together unless otherwise indicated. All patent and literature references cited in the present specification are hereby incorporated by reference in their entirety.

When a structural formula or chemical name is understood by the skilled person to have chiral centers, yet no chirality is indicated, for each chiral center individual reference is made to all three of either the racemic mixture, the pure R enantiomer, and the pure S enantiomer.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components.

The use of a substance as a medicament as described in this document can also be interpreted as the use of said substance in the manufacture of a medicament. Similarly, whenever a substance is used for treatment or as a medicament, it can also be used for the manufacture of a medicament for treatment. Compounds or compositions according to this invention are preferably for use in methods or uses according to this invention.

The word "about" or "approximately" when used in association with a numerical value (e.g. about 10) preferably means that the value may be the given value (of said 10) more or less 1% of the value.

The following examples are offered for illustrative purposes only, and are not intended to limit the scope of the present invention in any way

EXAMPLES

Example 1

Method for Preparing a Solution

This protocol describes the preparation of a 50 mg/mL solution of clozapine suitable for oral administration. Following, this procedure ensures a reproducible production of the oral solution. The following materials and equipment are used for the preparation of the oral solution of clozapine:

Materials

Polyethylene glycol 400: Merck EMPROVE® Ph Eur, JP grade (<30 ppm formaldehyde)

Peppermint oil: FCC (FDA 21 CFR (172.230))

Sucralose: Merck EMPROVE® exp Ph Eur,NF

Clozapine: Fagron

Equipment

IKA upper stirrer or equivalent

Top load balance capable of reading to at least 0.01 g

This practice describes the preparation of 500 mL solution of clozapine. The procedure is as follows:

Weigh, accurately, 25.0 grams of clozapine in a 500 mL amber glass sample jar.

Add, accurately weighed, 530.0 grams of polyethylene glycol 400 and stir the solution, using an IKA upper stirrer at 500 RPM for 2 hours until a clear solution is obtained.

Then add 0.50 grams of sucralose and 0.50 grams of peppermint oil and stir for an additional 2 hours until a clear solution is obtained.

Example 2

Identification, Assay and Purity of Clozapine in a 50 mg/ml Solution by HPLC This example describes a method for identification, assay and purity of clozapine in a solution as prepared in Example 1, using HPLC methods.

Materials

The following materials were used (note: appropriate alternative materials of comparable quality may be used):

Potassium di-hydrogen phosphate anhydrous ($KH_2PO_4$), reagent grade

Acetonitrile (MeCN); HPLC grade

Methanol [MeOH], HPLC grade

Water, ultrapure (Milli-Q); HPLC grade ortho-phosphoric acid 85% [m/m] ($H_3PO_4$), reagent grade Clozapine reference standard System suitability check sample; clozapine for peak identification, containing clozapine and impurities A, B, C and D. (product no. CRS Id. 00B621 of EDQM)

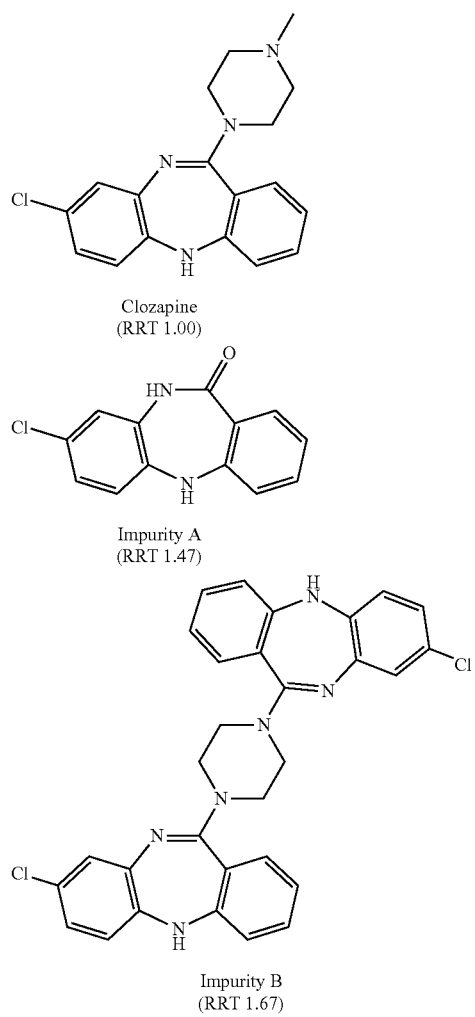

Clozapine
(RRT 1.00)

Impurity A
(RRT 1.47)

Impurity B
(RRT 1.67)

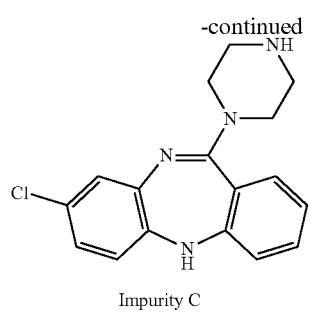

Impurity C
(norclozapine, RRT 0.91)

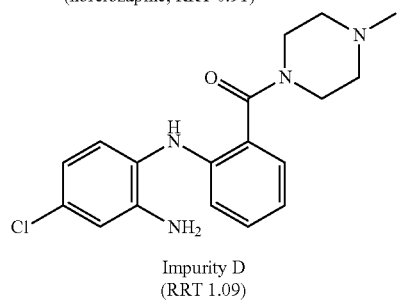

Impurity D
(RRT 1.09)

Apparatus

Note: an appropriate alternative apparatus of comparable quality may be used.

HPLC, with column heater and temperature controlled autosampler

Analytical column, Luna C18 (2), (Phenomenex, 150×4.6 mm, $d_p$=5 mm)

Guard column, SecurityGuard C18 (Phenomenex 4×3.0 mm)

Mechanical shaker

Analytical balance capable of reading to at least 0.01 mg

Top load balance capable of reading to at least 0.01 g

Ultrasonic bath pH meter

Positive displacement pipette 100-1000 µL

Mobile Phase and Solvent Solution Preparations

Note: The volume of the solvent solution, mobile phase and buffers may be scaled up or down as needed.

Mobile phase A; Phosphate buffer pH 2.5: dissolve approximately 4.1 g of $KH_2PO_4$ (15 mM) in 2 L of water. Adjust, if necessary, to pH 2.5±0.1 with phosphoric acid.

Mobile phase B: prepare a mixture of methanol and acetonitrile at a ratio of 50:50 [V/V].

Solvent Solution: Prepare a mixture of methanol and Milli-Q water at a ratio of 80:20 [V/V].

Standard and Sample Preparation

Note: The volume of the system suitability check preparation and of the standard preparations may be scaled up as needed.

System Suitability Check Preparation: prepare a system suitability check solution of clozapine for peak identification. Therefore, pipette 1.0 mL of Solvent Solution to the vial containing the suitability check sample and dissolve (the complete sample, 0.41 mg) by ultrasonication for 5 minutes. Aliquot the solution, in volumes of 100 µL in ten separate insert vials. Use one vial for this check and store the remaining vials in the fridge at −20° C. for future use.

Note: The System Suitability Check Preparation is stable for at least 48 hours (2 days) stored in dark at ambient temperature and in auto sampler at ambient temperature. Furthermore, the system suitability check sample is stable for at least two months at −20° C.

Standard Preparation: prepare a standard solution equivalent to approximately 0.30 mg clozapine per mL. Therefore, weigh approximately 15.0 mg of clozapine reference standard, accurately (p mg), into an amber volumetric flask of 50 mL (VRS). Add 30 mL solvent solution. Dissolve using an ultrasonic bath for 5 minutes, fill up to volume with solvent solution and homogenize.

Note: The Standard Preparation is stable for 120 hours (5 days) in refrigerator (2-8° C./dark) and for at least 48 hours (2 days) stored at ambient temperature and in an autosampler at ambient temperature. Prepare the standard preparation in duplicate (Std A and Std B).

Threshold Preparation: dilute the Standard Preparation to an equivalent of approximately 0.30 μg clozapine per mL (0.10%). Therefore, pipette 2.0 mL Standard Preparation A into a volumetric flask of 100 mL, fill up to volume with Solvent solution and homogenize. Pipette from this solution 1.0 mL into a 20 mL amber volumetric flask, fill up to volume with Solvent solution and homogenize.

Sample Preparation 0.3 mg/mL: transfer approximately 3.38 g (3 mL) of a 50 mg/mL clozapine solution, accurately weighed (q mg), into an amber volumetric flask of 50 mL (VS). Add approximately 40 mL of Solvent solution and place the flask on a mechanical shaker for approximately 10 min at 150 rpm. Fill up to volume with Solvent solution and homogenize. Pipette 5.0 mL (VS_pip1) into an amber volumetric flask of 50 mL (VS_flask1), fill up to volume with Solvent solution and homogenize (equivalent to 0.3 mg clozapine per mL).

Note: The Sample Preparation is stable for at least 48 hours (2 days) stored in dark at ambient temperature and in auto sampler at ambient temperature.

Placebo Preparation: transfer approximately 3.38 g (3 mL) of the placebo mix, accurately weighed (q mg), into an amber volumetric flask of 50 mL. Add approximately 40 mL of Solvent solution and place the flask on a mechanical shaker for approximately 10 min at 150 rpm. Fill up to volume with Solvent solution and homogenize. Pipette 5.0 mL into an amber volumetric flask of 50 mL, fill up to volume with Solvent solution and homogenize.

Note: The Placebo Preparation is stable for at least 48 hours (2 days) stored at ambient temperature and in an auto sampler at ambient temperature.

Instrumental Conditions

Analytical column: Luna C18 (2), (Phenomenex) 150×4.6 mm, $d_p$=5 μm

Guard column: Security Guard C18, (Phenomenex) 4×3.0 mm

| Gradient program: | Time [min] | Mobile phas A [%] | Mobile phase B [%] |
|---|---|---|---|
| | 0 | 80 | 20 |
| | 4 | 80 | 20 |
| | 24 | 20 | 80 |
| | 29 | 20 | 80 |
| | 30 | 80 | 20 |
| | 35 | 80 | 20 |

Mobile phase A: Phosphate buffer pH 2.5; Mobile phase B: Methanol/Acetonitrile=50:50 [V/V];

Column temperature: 30° C.; Flow: 1.2 mL/min; Autosampler temperature: 25° C.; Autosampler flush solvent: Acetonitrile/Milli-Q water=90:10 [V/V]; Seal wash Milli-Q water/Isopropanol=90:10 [V/V];

Detection: UV, 257 nm; //second ID: Scan conditions: 200-400 nm; Injection volume: 10 μL; Run time: 35 minutes.

Calculations

All calculations on the Sample Preparations are performed with the average peak area of the Standard Preparation injected over the whole sequence. Integrate the clozapine peak in the Sample Preparation (batch x, weighing 1). Calculate the assay of clozapine in mg per mL solution and percentage of label claim (% LC) with these equations:

$$C_{clo} \text{ [mg/mL solution]} = ((A_S \times V_S)/q) \times ((p \times P_{RS} \times V_{S\_Flask1} \times \rho)/(A_{RS} \times V_{RS} \times V_{S\_pip1} \times 100))$$

$$\% \text{ LC} = (C_{CLO}/\text{LC}) \times 100\%$$

$A_{RS}$=average peak area of clozapine in the Standard Preparation injected over the whole sequence; $A_S$=peak area of clozapine in the Sample Preparation; LC=label claim [mg/mL solution]; p=weight of clozapine Reference Standard in the Standard Preparation [mg]; $P_{RS}$=purity "as is" of clozapine in the Reference Standard [%]; q=volume of composite used for the Sample Preparation under investigation [mL]; $V_S$=volume of Sample Preparation [mL]; $V_{RS}$=volume of Standard Preparation [mL]; $V_{S\_Flask1}$=volume of dilution Sample Preparation [mL]; $V_{S\_pip1}$=Pipetted dilution volume of the Sample Preparation [mL]; ρ=Density of the sample preparation (1.12809 g/cm3); Repeat the calculation procedure with all remaining preparations of the batch.

Identify each impurity peak in the Sample Preparation (weighing 1, batch x) in comparison with the relative retention times in the System Suitability Check Preparation chromatogram. Disregard any peaks resulting from the injection of sham Preparation. Calculate the content of impurity I (CI) in % with the following equation:

$$\text{CI [\%]} = ((A_I \times V_S)/(q \times \text{LC})) \times ((p \times P_{RS} \times V_{S\_Flask1} \times \rho)/(A_{RS} \times V_{RS} \times V_{S\_pip1}) \times 100 \times \text{RRF}_I)) \times 100\%$$

In addition to the terms as defined above, AI=peak area of impurity I in the Sample Preparation injection; $\text{RRF}_I$=Relative Response Factor of impurity I; the Relative Response Factor ($\text{RRF}_I$) values for the individual impurities is 1.0 for all, except for impurity D, which is 2.7.

Reporting

The average total impurities for each batch are calculated by summing up the average content of single impurities for the batch greater than the Reporting Threshold (≤0.10%). The full accuracy of the individual results are used to determine the total impurities. If no impurity is present above the Reporting Threshold, then it is stated that the content of the total impurities: is ≤0.10%. If the average content of single impurities is below 1.0%, the content is reported as rounded to two decimal places; at and above 1.0%, the content is reported rounded to one decimal place.

Example 3

Solubility of Clozapine

For clozapine, solutions of 20 mg/mL or more are preferred for oral administration of the solution. For soft gel capsules an even higher concentration is preferable. Therefore, a solubility study for clozapine was performed. An excess of clozapine was weighed in a HPLC vial and 1.0 mL of various solvent systems was added. Following, the mixture was placed on a mechanical shaker for 24 hours at 200 RPM and analysed by HPLC for clozapine content. Results are shown in table 1:

TABLE 1 clozapine content in different solvent systems after 24 hours.

| Solvent system | Clozapine (mg/mL) | Solvent system | Clozapine (mg/mL) |
|---|---|---|---|
| 50% solutol in water | 17.8 | 100% Transcutol P | 151.3 |
| 20% kolliphor RH40 in water | 7.4 | 20% Transcutol P in PEG400 | 99.5 |
| N,N'-dimethyl acetamide (DMA) | 106.8 | 10% Transcutol P in PEG400 | 91.3 |
| N-methyl-2-pyrrolydone (NMP) | 409.7 | 5% Transcutol P in PEG400 | 91.8 |
| PEG400/Citrate buffer pH 4.0; 90:10 (V/V) | 56.2 | 50% solutol/PEG400 (10:90) | 81.6 |
| PEG400/Citrate buffer pH 4.0; 80:20 (V/V) | 44.6 | PEG400/34 mmol Citrate buffer; 80:20 (V/V) | 49.8 |
| PEG400/Citrate buffer pH 4.0; 70:30 (V/V) | 32.1 | PEG400/34 mmol Citrate buffer; 60:40 (V/V) | 47.6 |
| PEG400/Citrate buffer pH 4.0; 60:40 (V/V) | 29.6 | PEG400/34 mmol Citrate buffer; 40:60 (V/V) | 52.3 |
| PEG400/Citrate buffer pH 4.0; 50:50 (V/V) | 33.4 | PEG400/34 mmol Citrate buffer; 20:80 (V/V) | 52.7 |
| 0.1% acetic acid in water | 4.7 | Citrate buffer pH 4.7 | 19.9 |
| 1% acetic acid in water | 38.1 | Citrate buffer pH 4.0 | 34.3 |
| 5% acetic acid in water | 51.5 | Citrate buffer pH 3.7 | 44.0 |
| 10% acetic acid in water | 59.8 | Citrate buffer pH 3.4 | 57.2 |
| 1% citric acid in water | 27.6 | water | 0.3 |
| 5% citric acid in water | 34.2 | PEG400 | 77.0 |
| 10% citric acid in water | 50.7 | PEG400/water (80:20) | 31.1 |
| 40% corn oil in miglyol | 8.4 | PEG400/water (70:30) | 14.0 |
| Corn oil | 5.1 | PEG400/water (60:40) | 6.5 |
| miglyol | 10.3 | PEG400/water (50:50) | 2.3 |
| 20% Kolliphor RH40/PEG400 (10:90) | 72.8 | Caprylocaproyl macrogol-8 glycerides (Labrasol ®) | 34.0 |
| glycerol | 0.5 | PEG600/water (90:10) | 65.2 |
| ethanol | 33.9 | PEG200 | 81.8 |

Example 4

Effect of Sweetening Agents or Flavouring Agents on Clozapine Stability

The following solutions were prepared:

| Name | Contents |
|---|---|
| None | 50 mg/mL clozapine solution in PEG400 |
| Sucra | 50 mg/mL clozapine solution in PEG400, 0.05% sucralose |
| Mint | 50 mg/mL clozapine solution in PEG400, 0.05% peppermint oil |
| Both | 50 mg/mL clozapine solution in PEG400, 0.05% sucralose, 0.05% peppermint oil |

Solutions were stored at 25° C. with 60% relative humidity, or at 40° C. with 75% relative humidity. Table 2 shows the assay values for clozapine after several months:

TABLE 2 clozapine levels with various flavouring additives

| | | 0 months | | 1 month | | 2 months | | 3 months | | 6 months | |
|---|---|---|---|---|---|---|---|---|---|---|---|
| Name | °C. | Assay | RSD | Assay | RSD | Assay | RSD | Assay | RSD | Assay | RSD |
| None | 40 | 99.1 | 2.98 | 98.9 | 1.96 | 96.5 | 0.8 | 96.5 | 0.21 | 96.4 | 0.1 |
| | 25 | 99.1 | 2.98 | 99.9 | 0.19 | 100.0 | 1.2 | 99.0 | 0.10 | 99.1 | 0.2 |
| Sucra | 40 | 101.1 | 0.23 | 99.6 | 0.15 | 99.8 | 0.4 | 99.0 | 0.2 | 98.8 | 0.2 |
| | 25 | 101.1 | 0.23 | 100.0 | 0.32 | 100.6 | 0.0 | 99.8 | 0.1 | 100.1 | 0.0 |
| Mint | 40 | 100.9 | 0.20 | 99.0 | 0.16 | 99.4 | 0.0 | 98.5 | 0.1 | 98.5 | 0.1 |
| | 25 | 100.9 | 0.20 | 99.6 | 0.08 | 99.9 | 0.1 | 98.7 | 1.0 | 99.8 | 0.1 |
| Both | 40 | 100.6 | 0.31 | 99.4 | 0.13 | 99.5 | 0.4 | 98.7 | 0.2 | 98.3 | 0.3 |
| | 25 | 100.6 | 0.31 | 99.8 | 0.04 | 100.3 | 0.2 | 99.6 | 0.2 | 100.1 | 0.1 |

After 12 months, solutions "sucra", "mint", and "both" assayed clozapine levels at 98.8(0.1), 98.0(0.5), and 98.2 (0.4) respectively at 25° C. with 60% relative humidity. After 14 months under the same conditions, "none" assayed at 97.7(0.1).

Total impurities as described above were also assayed, as well as the amount of N-oxide. Table 3 shows the assay values for impurities and N-oxide after several months:

TABLE 3 impurity levels with various flavouring additives

| Name | °C. | 0 months | | 1 month | | 2 months | | 3 months | | 6 months | |
|---|---|---|---|---|---|---|---|---|---|---|---|
| | | Impurity | N | Impurity | N | Impurity | N | Impurity | N | Impurity | N |
| None | 40 | <0.05 | <0.05 | 0.36 | 0.36 | 0.44 | 0.41 | 0.50 | 0.45 | 0.60 | 0.50 |
|  | 25 | <0.05 | | 0.29 | | 0.33 | | 0.35 | | 0.37 | |
| Sucra | 40 | 0.29 | 0.29 | 0.57 | 0.53 | 0.62 | 0.57 | 0.68 | 0.62 | 0.77 | 0.69 |
|  | 25 | 0.29 | | 0.46 | | 0.47 | | 0.49 | | 0.55 | |
| Mint | 40 | 0.29 | 0.29 | 0.60 | 0.56 | 0.68 | 0.62 | 0.78 | 0.70 | 0.95 | 0.84 |
|  | 25 | 0.29 | | 0.46 | | 0.48 | | 0.51 | | 0.52 | |
| Both | 40 | 0.29 | 0.29 | 0.59 | 0.56 | 0.66 | 0.61 | 0.75 | 0.68 | 0.89 | 0.80 |
|  | 25 | 0.29 | | 0.47 | | 0.48 | | 0.51 | | 0.56 | |

After 12 months, solutions "sucra", "mint", and "both" assayed impurities at 0.52, 0.56, and 0.55 respectively at 25° C. with 60% relative humidity. After 14 months under the same conditions, "none" assayed at 0.43.

Example 5

Effect of Oxygen Purging on Clozapine Stability

The following 50 mg/mL clozapine solutions were prepared:

| Name | Contents |
|---|---|
| None | PEG400 |
| Flavour | PEG400, 0.05% sucralose, 0.05% peppermint oil |
| None $N_2$ | PEG400 purged with $N_2$, solution prepared under $N_2$ flow |
| Flavour $N_2$ | PEG400, 0.05% sucralose, 0.05% peppermint oil, purged with $N_2$, under $N_2$ flow |

Solutions were stored at 40° C. with 75% relative humidity (RH). Table 4 shows the assay values for clozapine after several months, and table 5 shows impurity levels and N-oxide levels:

TABLE 4 clozapine levels with or without oxygen exclusion

| Name | °C. | 0 months | | 1 month | | 2 months | | 3 months | | 6 months | |
|---|---|---|---|---|---|---|---|---|---|---|---|
| | | Assay | RSD | Assay | RSD | Assay | RSD | Assay | RSD | Assay | RSD |
| None | 40 | 100.3 | 0.05 | 99.9 | 0.44 | 99.4 | 0.0 | 99.4 | 0.0 | 99.0 | 0.2 |
| Flavour | 40 | 99.7 | 0.14 | 99.2 | 0.32 | 98.3 | 0.1 | 98.5 | n.d. | 98.1 | 0.2 |
| None $N_2$ | 40 | 100.0 | 0.13 | 99.5 | 0.02 | 98.9 | 0.2 | 99.1 | 0.2 | 98.4 | 0.1 |
| Flavour $N_2$ | 40 | 99.5 | 0.21 | 98.3 | 0.37 | 98.5 | 0.0 | 98.0 | 0.4 | 97.6 | 0.4 |

TABLE 5 impurity levels with or without oxygen exclusion at 40° C./75% RH

| Name | 0 months | | 1 month | | 2 months | | 3 months | | 6 months | |
|---|---|---|---|---|---|---|---|---|---|---|
| | Impurity | N | Impurity | N | Impurity | N | Impurity | N | Impurity | N |
| None | 0.07 | 0.07 | 0.58 | 0.58 | 0.69 | 0.63 | 0.74 | 0.67 | 0.85 | 0.76 |
| Flavour | 0.08 | 0.08 | 0.59 | 0.59 | 0.71 | 0.65 | 0.76 | 0.69 | 0.95 | 0.79 |
| None $N_2$ | 0.06 | 0.06 | 0.58 | 0.58 | 0.68 | 0.63 | 0.72 | 0.66 | 0.83 | 0.75 |
| Flavour $N_2$ | 0.04 | <0.05 | 0.59 | 0.59 | 0.70 | 0.65 | 0.75 | 0.69 | 0.93 | 0.78 |

Example 6

Effect of Antioxidants on Clozapine Stability and Impurity Levels

The following 50 mg/mL clozapine solutions with 0.05% sucralose and 0.05% peppermint oil were prepared, using clozapine from Fagron unless indicated otherwise:

| Name | Contents |
|---|---|
| Fagron | PEG400 (using PEG from supplier Fagron (Nazareth, Belgium)) |
| Nobilus | PEG400 (using PEG from supplier Nobilus Ent (Kutno, Poland)) |
| 90:10 | 90% PEG600, 10% H$_2$O |
| 90:10 thio | 90% PEG600, 10% H$_2$O, 0.1% thiosulphate, 0.1% tocopherol |
| 88:12 thio | 88% PEG600, 10% H$_2$O, 0.1% thiosulphate, 0.1% tocopherol, 2% Transcutol P |

The tocopherol that was used was α-tocopherol-PEG-succinate. The PEG600 solutions were seen to solidify during storage at 15° C. After melting at room temperature, no solids were observed. Solutions were stored at 25° C. with 60% relative humidity, and at 40° C. with 75% relative humidity (RH). Table 6 shows the assay values for clozapine after several months, and table 7 shows impurity levels and N-oxide levels:

TABLE 6 clozapine levels with or without antioxidants

| | | 0 months | | 1 month | | 2 months | | 6 months | | 12 months | |
|---|---|---|---|---|---|---|---|---|---|---|---|
| Name | ° C. | Assay | RSD | Assay | RSD | Assay | RSD | Assay | RSD | Assay | RSD |
| Fagron | 40 | 100.6 | 0.19 | 100.0 | 0.01 | 98.3 | 0.11 | 98.6 | 0.10 | 98.6 | 0.12 |
|  | 25 | 100.6 | 0.19 | 100.7 | 0.04 | 99.7 | 0.07 | 99.8 | 0.37 | 100.4 | 0.24 |
| Nobilus | 40 | 100.2 | 0.32 | 100.6 | 0.24 | 99.6 | 0.00 | 98.2 | 0.04 | 98.0 | 0.02 |
|  | 25 | 100.2 | 0.32 | 100.4 | 0.27 | 99.6 | 0.07 | 99.0 | 0.14 | 99.7 | 0.14 |
| 90:10 | 40 | 101.2 | 0.15 | 101.2 | 0.07 | 100.4 | 0.08 | 99.0 | 0.37 | 98.4 | 0.01 |
|  | 25 | 101.2 | 0.15 | 101.4 | 0.21 | 100.4 | 0.26 | 99.7 | 0.44 | 100.5 | 0.01 |
| 90:10 thio | 40 | 101.3 | 0.28 | 101.8 | 0.07 | 100.9 | 0.08 | 100.0 | 0.14 | 99.7 | 0.14 |
|  | 25 | 101.3 | 0.28 | 101.1 | 0.76 | 100.8 | 0.02 | 100.2 | 0.43 | 101.0 | 0.14 |
| 88:12 thio | 40 | 101.8 | 0.76 | 102.7 | 0.04 | 101.7 | 0.18 | 100.6 | 0.04 | 100.7 | 0.22 |
|  | 25 | 101.8 | 0.76 | 102.0 | 0.32 | 101.9 | 0.10 | 100.9 | 0.45 | 101.9 | 0.05 |

Total impurities as described above were also assayed, as well as the amount of N-oxide. Table 7 shows the assay values for impurities and N-oxide after several months:

TABLE 7 impurity levels with or without antioxidants

| | | 0 months | | 1 month | | 2 months | | 6 months | | 12 months | |
|---|---|---|---|---|---|---|---|---|---|---|---|
| Name | ° C. | Impurity | N | Impurity | N | Impurity | N | Impurity | N | Impurity | N |
| Fagron | 40 | 0.08 | 0.08 | 0.27 | 0.27 | 0.32 |  | 0.59 |  | 0.81 |  |
|  | 25 | 0.08 |  | 0.20 |  | 0.22 |  | 0.26 |  | 0.39 |  |
| Nobilus | 40 | 0.08 | 0.08 | 0.25 | 0.25 | 0.30 |  | 0.51 |  | 0.77 |  |
|  | 25 | 0.08 |  | 0.19 |  | 0.21 |  | 0.27 |  | 0.35 |  |
| 90:10 | 40 | 0.14 | 0.13 | 0.23 | 0.23 | 0.26 |  | 0.62 |  | 1.25 |  |
|  | 25 | 0.14 |  | 0.20 |  | 0.21 |  | 0.23 |  | 0.31 |  |
| 90:10 thio | 40 | <0.05 | <0.05 | <0.05 | <0.05 | <0.05 |  | 0.14 |  | 0.45 |  |
|  | 25 | <0.05 |  | <0.05 |  | <0.05 |  | <0.05 |  | <0.05 |  |
| 88:12 thio | 40 | <0.05 | <0.05 | <0.05 | <0.05 | <0.05 |  | 0.05 |  | 0.34 |  |
|  | 25 | <0.05 |  | <0.05 |  | <0.05 |  | <0.05 |  | <0.05 |  |

Antioxidants do not appear to influence clozapine levels within assay sensitivity, but the formation of impurities is inhibited. More solutions were prepared to assay the effect of antioxidants on impurity formation. The following 50 mg/mL clozapine solutions with 0.05% sucralose and 0.05% peppermint oil were prepared, using clozapine from Fagron and α-tocopherol-PEG-succinate as a tocopherol when indicated:

| Name | Contents |
|---|---|
| 400 | 100% PEG400 |
| Toc | 100% PEG400 and tocopherol |
| Thio Toc | 90% PEG400, 10% $H_2O$, 0.1% thiosulphate, 0.1% tocopherol |
| Thio Gal | 90% PEG400, 10% $H_2O$, 0.1% thiosulphate, 0.1% propyl gallate |

Solutions were stored at 25° C. with 60% relative humidity, and at 40° C. with 75% relative humidity (RH). Table 8 shows the assay values for clozapine after several months, and table 9 shows impurity levels and N-oxide levels:

TABLE 8 clozapine levels with or without antioxidants

| Name | ° C. | 0 months Assay | RSD | 1 month Assay | RSD | 2 months Assay | RSD | 3 months Assay | RSD | 8 months Assay | RSD |
|---|---|---|---|---|---|---|---|---|---|---|---|
| 400 | 40 | 99.9 | 0.23 | 99.9 | 0.02 | | | | | 98.9 | 0.10 |
| | 25 | | | | | | | | | | |
| Toc | 40 | 99.7 | 0.08 | 99.0 | 0.02 | | | | | 98.1 | 0.02 |
| | 25 | | | | | | | | | | |

Total impurities as described above were also assayed, as well as the amount of N-oxide. Table 9 shows the assay values for impurities and N-oxide after several months:

TABLE 9 impurity levels with or without antioxidants

| Name | ° C. | 0 months Impurity | N | 1 month Impurity | N | 2 months Impurity | N | 3 months Impurity | N | 8 months Impurity | N |
|---|---|---|---|---|---|---|---|---|---|---|---|
| 400 | 40 | 0.07 | 0.07 | 0.71 | | 0.82 | | | | 1.1 | 1.01 |
| | 25 | | | | | | | | | | |
| Toc | 40 | 0.07 | 0.07 | 0.68 | | 0.73 | | | | 1.1 | 1.01 |
| | 25 | | | | | | | | | | |
| Thio Toc | 40 | <0.05 | <0.05 | <0.05 | <0.05 | 0.14 | 0.09 | 0.23 | 0.07 | <0.05 | |
| | 25 | <0.05 | | <0.05 | | 0.07 | | 0.07 | | | |
| Thio Gal | 40 | | 0.10 | 0.28 | 0.28 | 0.52 | 0.47 | | | | |
| | 25 | | | 0.15 | | 0.25 | | 0.3 | | | |

Experiments using meglumine ((2R,3R,4R,5S)-6-(Methylamino)hexane-1,2,3,4,5-pentol) as an excipient did not result in solutions with an improved stability. Impurity levels of over 0.80 percent were detected in a matter of hours.

Example 7

Viscosity of Clozapine Formulations

The viscosity of some solutions was determined using a viscosimeter (HAAKE Viscotester C, settings: spindle 3, 200 RPM). Results are shown in table 10:

TABLE 10 viscosity of solutions

| Solution | ° C. | RPM | Viscosity (cP) |
|---|---|---|---|
| 50 mg/mL clozapine in PEG400 | 15 | 200 | 267.7 |
| | 20 | | 214.4 |
| | 25 | | 176.5 |
| PEG400 | 25 | 50 | 126.1 |
| | | 60 | 128.1 |
| | | 100 | 140.4 |
| PEG600/ water (90:10) | 25 | 50 | 163.1 |
| | | 60 | 164.8 |
| | | 100 | 175.5 |

Reference Example 8

Unstable Formulations

Experiments using meglumine ((2R,3R,4R,5S)-6-(Methylamino)hexane-1,2,3,4,5-pentol) as an excipient did not result in solutions with an improved stability. Impurity levels of over 0.80 percent were detected in a matter of hours. Also the following formulations were prepared and the stability of these formulations (shown in tables 11 and 12) was tested at 40° C./75% RH:

1. 50 mg/mL clozapine solution in a 10% citric acid in water
2. 50 mg/mL clozapine solution in a 5% acetic acid in water
3. 50 mg/mL clozapine solution in a 10% citric acid in water/PEG400 (20:80, V/V)
4. 50 mg/mL clozapine solution in citrate buffer pH 3.5/PEG400 (80:20, V/V)+acesulfam K
5. 50 mg/mL clozapine solution in citrate buffer pH 3.5 with menthol
6. 50 mg/mL clozapine solution in citrate buffer pH 3.5/PEG400 (80:20, V/V)+menthol
7. 25 mg/mL clozapine solution in citrate buffer pH 3.5/PEG400 (80:20, V/V)+acesulfam K 8. 25 mg/mL clozapine solution in citrate buffer pH 3.5/PEG400 (80:20, V/V)+menthol

TABLE 11 clozapine levels in unstable solutions as reference examples

| Sample (#) | Clozapine t = 0 months | | Clozapine t = 1 month | | Clozapine t = 2 months | | Clozapine t = 3 months | | Clozapine t = 6 months | |
|---|---|---|---|---|---|---|---|---|---|---|
| | Assay (%) | RSD (%) | Assay (%) | RSD (%) | Assay (%) | RSD (%) | Assay(%) | RSD (%) | Assay(%) | RSD (%) |
| 1 | 102.3 | 3.43 | 30.3 | 0.55 | 4.8 | 0.6 | 1.3 | 1.04 | 0.6 | 0.4 |
| 2 | 99.5 | 1.18 | 64.3 | 0.29 | 32.3 | 2.2 | 15.3 | 0.02 | 1.0 | 3.7 |
| 3 | 96.3 | 0.32 | 88.5 | 0.67 | 86.8 | 1.4 | 84.6 | 0.13 | 80.2 | 0.5 |
| 4 | 99.2 | 0.12 | 70.5 | 0.01 | stopped | | | | | |
| 5 | 98.6 | 0.22 | 36.9 | 8.03 | stopped | | | | | |
| 6 | 99.2 | 0.19 | 69.8 | 0.69 | stopped | | | | | |
| 7 | 100.6 | 0.21 | 51.5 | 0.33 | stopped | | | | | |
| 8 | 102.7 | 0.40 | 52.3 | 0.10 | stopped | | | | | |

TABLE 12 impurity levels in unstable solutions as reference examples

| Sample (#) | t = 0 | t = 1 month | t = 2 months | t = 3 months | t = 6 months |
|---|---|---|---|---|---|
| | | | Total impurities (%) | | |
| 1 | <0.05 | 3.52 | 2.87 | 1.93 | 2.27 |
| 2 | <0.05 | 2.13 | 1.64 | 1.21 | 1.57 |
| 3 | <0.05 | 1.21 | 2.46 | 3.38 | 5.60 |
| 4 | 1.06 | 7.08 | stopped | | |
| 5 | 0.47 | 3.17 | stopped | | |
| 6 | 0.40 | 6.69 | stopped | | |
| 7 | 1.66 | 8.24 | stopped | | |
| 8 | 0.59 | 7.35 | stopped | | |

The invention claimed is:

1. A composition comprising a solvent system and a substance of general formula (I)

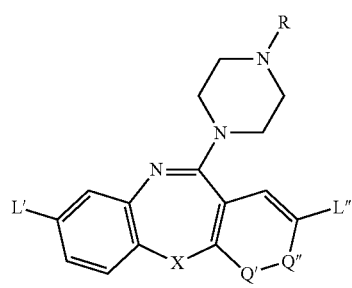

(I)

or a pharmaceutically acceptable salt thereof, wherein
X is —O—, —S—, or —N(H)—,
R is —H, —CH₃, or —(CH₂)₂—O—(CH₂)₂—OH,
L' and L" are each independently chosen from the group consisting of —H, —CH₃, and halogen, wherein halogen is preferably chlorine,
Q' and Q" together form —CH=CH— or —S—,
wherein the solvent system comprises
  a) 70-100% by weight of poly(ethylene glycol) with a number-average molecular weight of 1000 or less,
  b) 0-30% by weight of water,
wherein the composition is a solution, and
wherein the poly(ethylene glycol) comprises less than 30 μg/g of formaldehyde impurity.

2. The composition according to claim 1, wherein the substance of general formula (I) is selected from the group consisting of clozapine, norclozapine, olanzapine, norolanzapine, loxapine, amoxapine, clotiapine, quetiapine, and norquetiapine, or a pharmaceutically acceptable salt thereof.

3. The composition according to claim 1, comprising at least 11 mg/mL of the substance of general formula (I) or the pharmaceutically acceptable salt thereof.

4. The composition according to claim 1, further comprising at most 10 mg/mL by weight of flavouring or sweetening agents.

5. The composition according to claim 1, wherein the poly(ethylene glycol) has a number-average molecular weight of 200-800.

6. The composition according to claim 1, further comprising an antioxidant.

7. The composition according to claim 1, wherein the composition is a pharmaceutical composition.

8. The composition according to claim 1, further comprising a nonionic surfactant.

9. The composition according to claim 1, wherein the composition consists essentially of:
  i) the substance of general formula (I) or the pharmaceutically acceptable salt thereof, and
  ii) the solvent system consisting essentially of 70-100% by weight poly(ethylene glycol) with a number-average molecular weight of 1000 or less and 0-30% by weight of water, and
  iii) optionally one or more flavouring or sweetening agent, and
  iv) optionally one or more antioxidant.

10. A composition comprising a solvent system and a substance of general formula (I)

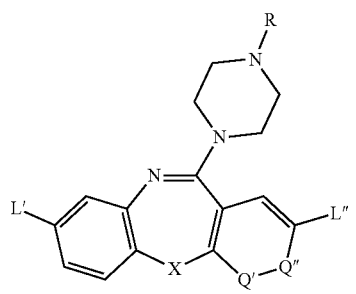

(I)

or a pharmaceutically acceptable salt thereof, wherein
X is —O—, —S—, or —N(H)—,
R is —H, —CH₃, or —(CH₂)₂—O—(CH₂)₂—OH, L' and L" are each independently chosen from the group consisting of —H, —CH₃, and halogen, Q' and Q" together form —CH═CH— or —S—, wherein the solvent system comprises
  a) 70-100% by weight of poly(ethylene glycol) with a number-average molecular weight of 1000 or less,
  b) 0-30% by weight of water, wherein the composition is a solution, and wherein the poly(ethylene glycol) comprises less than 80 μg/g of formaldehyde impurity, wherein the substance of general formula (I) or the pharmaceutically acceptable salt thereof is stable for at least one month.

11. A method of treating psychosis in a subject in need thereof, the method comprising administering to the subject an effective amount of the composition of claim 1.

12. The method of claim 11, wherein the composition is for oral administration.

13. The method of claim 12, wherein the oral administration is in a daily dose of at least 6 mg.

14. The method of claim 11, wherein the composition is for administration at least one time per day.

15. The composition according to claim 1, wherein the substance of general formula (I) is clozapine or a pharmaceutically acceptable salt thereof.

16. The composition according to claim 1, wherein the substance of general formula (I) or the pharmaceutically acceptable salt thereof is stable for at least one month.

17. The composition according to claim 1, comprising at least 70 mg/mL of the substance of general formula (I) or the pharmaceutically acceptable salt thereof.

18. The composition according to claim 10, wherein the substance of general formula (I) is clozapine or a pharmaceutically acceptable salt thereof.

19. The composition according to claim 10, wherein the substance of general formula (I) or the pharmaceutically acceptable salt thereof is stable for at least six months.

20. The composition according to claim 10, comprising at least 70 mg/mL of the substance of general formula (I) or the pharmaceutically acceptable salt thereof.

* * * * *